United States Patent [19]
Gallenkamp et al.

[11] Patent Number: 6,093,837
[45] Date of Patent: Jul. 25, 2000

[54] PROCESS FOR PREPARING 3-(1-HYDROXYPHENYL-1-ALKOXIMINOMETHYL) DIOXAZINES

[75] Inventors: Bernd Gallenkamp; Lothar Rohe, both of Wuppertal; Herbert Gayer, Monheim; Peter Gerdes, Aachen, all of Germany

[73] Assignee: Bayer Aktiengesellschaft, Leverkusen, Germany

[21] Appl. No.: 09/186,708

[22] Filed: Nov. 5, 1998

Related U.S. Application Data

[62] Division of application No. 08/982,531, Dec. 2, 1997, Pat. No. 6,005,104.

[30] Foreign Application Priority Data

Dec. 9, 1996 [DE] Germany .............................. 196 51 039
Feb. 19, 1997 [DE] Germany .............................. 197 06 396

[51] Int. Cl.$^7$ .................................................. C07D 307/82
[52] U.S. Cl. ................................................................ 549/467
[58] Field of Search .............................................. 549/467

[56] References Cited

U.S. PATENT DOCUMENTS 5,679,676 10/1997 Kruger et al. ........................ 514/229.2

*Primary Examiner*—Richard L. Raymond
*Attorney, Agent, or Firm*—Norris, McLaughlin & Marcus, P.A.

[57] ABSTRACT

The present invention relates to a novel process for preparing 3-(1-hydroxyphenyl-1-alkoximinomethyl)dioxazines which are known as intermediates for preparing compounds having fungicidal properties (WO 95-04728). Furthermore, the invention relates to novel 3-(1-hydroxyphenyl-1-alkoximinomethyl)dioxazines, to novel intermediates for their preparation and to a plurality of processes for preparing the novel intermediates.

4 Claims, No Drawings

PROCESS FOR PREPARING 3-(1-HYDROXYPHENYL-1-ALKOXIMINOMETHYL) DIOXAZINES

This application is a division of U.S. Ser. No. 08/982,531, which was filed on Dec. 2, 1997, now U.S. Pat. No. 6,005,104.

The present invention relates to a novel process for preparing 3-(1-hydroxyphenyl-1-alkoximinomethyl) dioxazines which are known as intermediates for preparing compounds having fungicidal properties (WO95-04728). Furthermore, the invention relates to novel 3-(1-hydroxyphenyl-1-alkoximinomethyl)dioxazines, to novel intermediates for their preparation and to a plurality of processes for preparing the novel intermediates.

It has already been disclosed that certain 3-(1-hydroxyphenyl-1-alkoximinomethyl)dioxazines can be prepared starting from the corresponding hydroxyphenyl acetates (cf. WO 95-04728). Thus, for example (5,6-dihydro[1,4,2]dioxazin-3-yl)-(2-hydroxyphenyl)-methanone-O-methyl oxime (1) can be prepared by reacting methyl hydroxyphenylacetate (a) with dihydropyrane, converting the resulting dihydropyranyl ether (b) with t-butyl nitrite into methyl 2-[2-(tetrahydropyran-2-yloxy)-phenyl]-2-hydroximinoacetate (c), alkylating this compound with iodomethane to give methyl 2-[2-(tetrahydropyran-2-yloxy)-phenyl]-2-methoximino-acetate (d), reacting this with hydroxylamine to give 2-[2-(tetrahydropyran-2-yloxy)-phenyl]-2-methoximino-N-hydroxyacetamide (e), cyclizing the latter with dibromoethane to give 3-{1-[2-(tetrahydropyran-2-yloxy)-phenyl]-1-methoximino-methyl}-5,6-dihydro-1,4,2-dioxazine (f), and finally removing the tetrahydropyranyl group using acid catalysis. This synthesis can be illustrated by the following scheme:

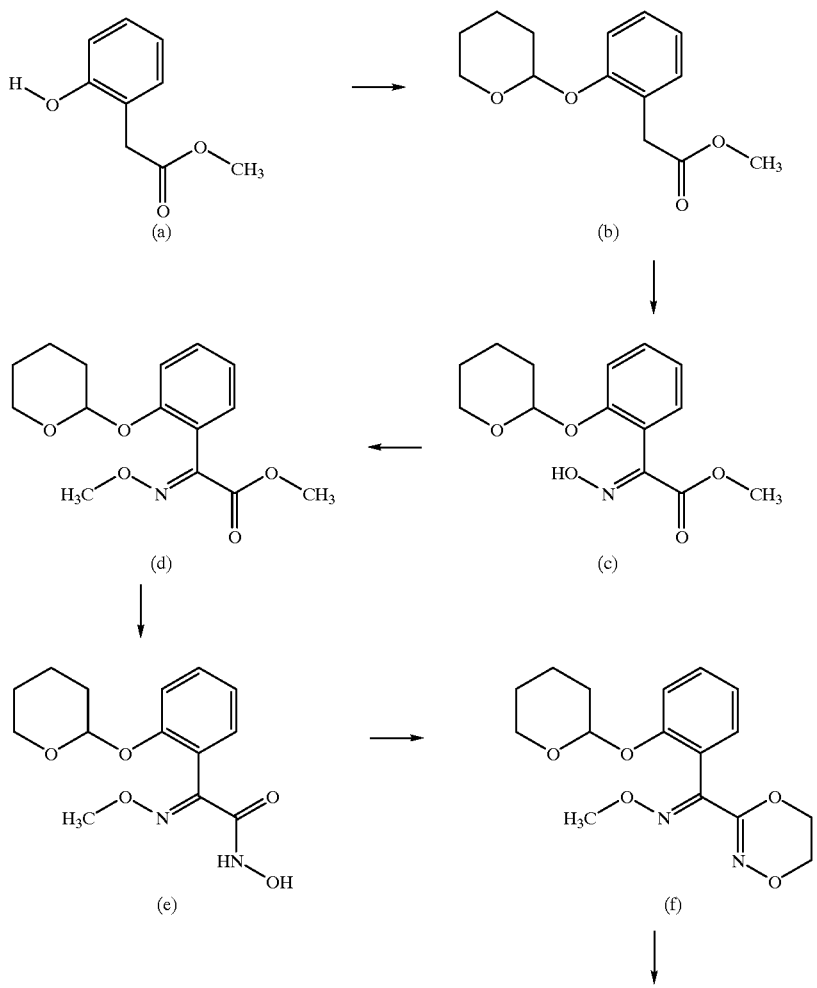

-continued

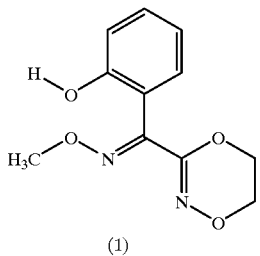

(1)

A major disadvantage of this process is the fact that a large number of steps must be carried out with occasional low yields, which has a decisively adverse effect on cost-efficiency.

It has now been found that novel and known 3-(1-hydroxyphenyl-1-alkoximinomethyl)dioxazines of the general formula (I)

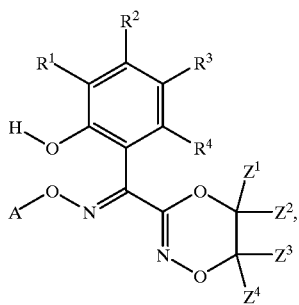

(I)

in which
A represents alkyl,
$R^1$, $R^2$, $R^3$ and $R^4$ are identical or different and each represents independently of the others hydrogen, halogen, cyano, nitro, in each case optionally halogen-substituted alkyl, alkoxy, alkylthio, alkylsulphinyl or alkylsulphonyl and
$Z^1$, $Z^2$, $Z^3$ and $Z^4$ are identical or different and each represents independently of the others hydrogen, alkyl, halogenoalkyl or hydroxyalkyl, or
$Z^1$ and $Z^2$, or $Z^1$ and $Z^3$, or $Z^3$ and $Z^4$, join with the respective carbon atoms to which they are attached to form a cycloaliphatic ring,
are obtained when (process a) O-hydroxyethyl-O'-alkyl-benzofurandione dioximes of the formula (II)

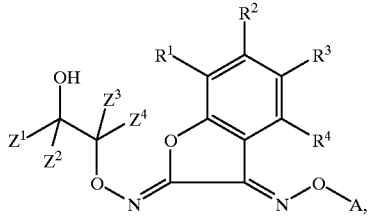

(II)

in which
A, $R^1$, $R^2$, $R^3$, $R^4$, $Z^1$, $Z^2$, $Z^3$ and $Z^4$ are each as defined above,
are rearranged, if appropriate in the presence of a diluent and, if appropriate, in the presence of a base or an acid, and the products obtained, which may be present as mixtures of stereoisomers, are, if appropriate, isomerized to give the desired E isomers, if appropriate in the presence of a diluent and, if appropriate, in the presence of an acid.

In the definitions, the saturated or unsaturated hydrocarbon chains, such as alkyl, including in combination with hetero atoms, such as in alkoxy or alkylthio, are in each case straight-chain or branched.

The compounds which are preparable according to the invention and their precursors may, if appropriate, be present as mixtures of various possible isomeric forms, in particular of stereoisomers such as, for example, E and Z isomers, and, if appropriate, also as tautomers. Both the E and Z isomers, and any mixtures of these isomers, and the possible tautomeric forms are claimed.

The method of process a) according to the invention is preferably employed for preparing compounds of the formula (I) in which
A represents methyl, ethyl, n- or i-propyl and
$R^1$, $R^2$, $R^3$ and $R^4$ are identical or different and each represents independently of the others hydrogen, halogen, cyano, nitro, or represents alkyl, alkoxy, alkylthio, alkylsulphinyl or alkylsulphonyl having in each case 1 to 6 carbon atoms, each of which is optionally substituted by 1 to 5 halogen atoms, and
$Z^1$, $Z^2$, $Z^3$ and $Z^4$ are identical or different and each represents independently of the others hydrogen, alkyl or hydroxyalkyl having in each case 1 to 4 carbon atoms or halogenoalkyl having 1 to 4 carbon atoms and 1 to five identical or different halogen atoms, or
$Z^1$ and $Z^2$, or $Z^1$ and $Z^3$, or $Z^3$ and $Z^4$, join with the respective carbon atoms to which they are attached to form a cycloaliphatic ring of five, six or seven carbon atoms.

Particular preference is given to preparing compounds of the formula (I) in which
A represents methyl or ethyl and
$R^1$, $R^2$, $R^3$ and $R^4$ are identical or different and each represents independently of the others hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl,
$Z^1$, $Z^2$, $Z^3$ and $Z^4$ are identical or different and each represents independently of the others hydrogen, methyl, ethyl, n- or i-propyl, n-, i-, s- or t-butyl, hydroxymethyl, trifluoromethyl or trifluoroethyl, or
$Z^1$ and $Z^2$, or $Z^1$ and $Z^3$, or $Z^3$ and $Z^4$, join with the respective carbon atoms to which they are attached to form a cycloaliphatic ring of five, six or seven carbon atoms.

The present invention also relates to novel 3-(1-hydroxyphenyl-1-alkoximinomethyl)dioxazines of the formula (I-a)

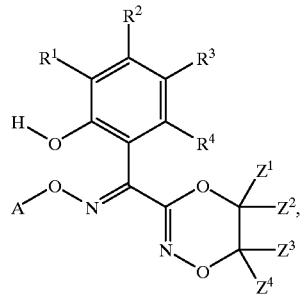

(I-a)

in which

A, $R^1$, $R^2$, $R^3$, $R^4$, $Z^1$, $Z^2$, $Z^3$ and $Z^4$ are each as defined above, but where at least one of the substituents $R^1$, $R^2$, $R^3$, $R^4$, $Z^1$, $Z^2$, $Z^3$ and $Z^4$ is different from hydrogen.

The abovementioned general or preferred radical definitions apply both to the compounds of the formula (I) and also, correspondingly, to the starting materials or intermediates required in each case for the preparation.

These radical definitions can be combined with each other at will, i.e. including combinations between the given ranges of preferred compounds.

The formula (II) provides a general definition of the O-hydroxyethyl-O'-alkyl-benzofurandione dioximes required as starting materials for carrying out the process a) according to the invention. In this formula (II), A, $R^1$, $R^2$, $R^3$, $R^4$, $Z^1$, $Z^2$, $Z^3$ and $Z^4$ each preferably or in particular have those meanings which have already been mentioned in connection with the description of the compounds of the formula (I) preparable according to the invention as being preferred or as being particularly preferred for A, $R^1$, $R^2$, $R^3$, $R^4$, $Z^1$, $Z^2$, $Z^3$ and $Z^4$.

The starting materials of the formula (II) have not been disclosed before, and as novel compounds they also form part of the subject matter of the present application.

The O-hydroxyethyl-O'-alkyl-benzofurandione dioximes of the formula (II) are obtained when process b) O-alkyl-benzofurandione dioximes of the formula (III)

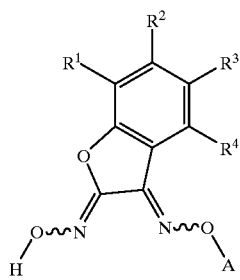

(III)

in which

A, $R^1$, $R^2$, $R^3$ and $R^4$ are each as defined above are reacted with an ethane derivative of the formula (IV)

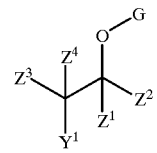

(IV)

in which $Y^1$ represents halogen, alkylsulphonyloxy, arylsulphonyloxy or alkanoyloxy and G represents hydrogen, or $Y^1$ and G are linked by a single bond, where $Y^1$ represents oxygen and G represents

or $Y^1$ and G together represent a single bond and $Z^1$, $Z^2$, $Z^3$ and $Z^4$ are each as defined above, if appropriate in the presence of a diluent and, if appropriate, in the presence of a base.

The formula (III) provides a general definition of the O-alkyl-benzofurandione dioximes required as starting materials for carrying out the process b) according to the invention. In this formula (III), $R^1$, $R^2$, $R^3$ and $R^4$ each preferably or in particular have those meanings which have already been mentioned in connection with the description of the compounds of the formula (I) preparable according to the invention as being preferred or as being particularly preferred for $R^1$, $R^2$, $R^3$ and $R^4$.

The starting materials of the formula (III) have not been disclosed before, and as novel compounds they also form part of the subject matter of the present application.

The O-alkyl-benzofurandione dioximes of the formula (III) are obtained when (process c) ω-nitro-2-hydroxyacetophenone oximes of the formula (V)

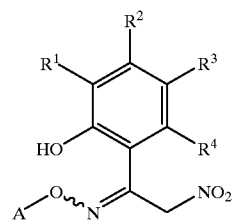

(V)

in which

A, $R^1$, $R^2$, $R^3$ and $R^4$ are each as defined above are reacted with a base, if appropriate in the presence of a diluent, or when (process d) O-alkyl-benzofuranone oximes of the formula (VI)

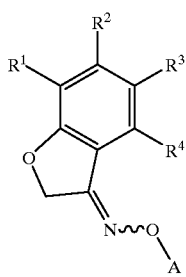

(VI)

in which

A, $R^1$, $R^2$, $R^3$ and $R^4$ are each as defined above are reacted with an alkali metal nitrite or an alkyl nitrite, if appropriate in the presence of a diluent and, if appropriate, in the presence of an acid or a base.

The formula (V) provides a general definition of the ω-nitro-2-hydroxyacetophenone oximes required as starting materials for carrying out the process c) according to the invention. In this formula (V), A, $R^1$, $R^2$, $R^3$ and $R^4$ each preferably or in particular have those meanings which have already been mentioned in connection with the description of the compounds of the formula (I) preparable according to the invention as being preferred or as being particularly preferred for A, $R^1$, $R^2$, $R^3$ and $R^4$.

The starting materials of the formula (V) have not been disclosed before, and as novel compounds they also form part of the subject matter of the present application.

The ω-nitro-2-hydroxyacetophenone oximes of the formula (V) are obtained when (process e) ω-nitro-2-hydroxyacetophenones of the formula (VII)

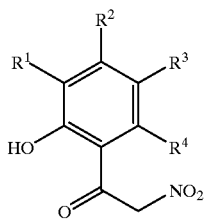

(VII)

in which $R^1$, $R^2$, $R^3$ and $R^4$ are each as defined above are reacted with an alkoxyamine of the formula (VIII)

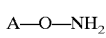

A—O—NH$_2$  (VIII)

in which

A is as defined above—or an acid addition complex thereof— if appropriate in the presence of a diluent and, if appropriate, in the presence of an acid acceptor.

The formula (VII) provides a general definition of the ω-nitro-2-hydroxyacetophenones required as starting materials for carrying out the process e) according to the invention. In this formula (VII), A, $R^1$, $R^2$, $R^3$ and $R^4$ each preferably or in particular have those meanings which have already been mentioned in connection with the description of the compounds of the formula (I) preparable according to the invention as being preferred or as being particularly preferred for A, $R^1$, $R^2$, $R^3$ and $R^4$.

The starting materials of the formula (VII) are known and can be obtained by known methods (Proc.-Indian Acad.Sci.Sect.A, 83, 1976, 238, 239, 242; J.Chem.Res.Miniprint, 1978, 865, 877; J.Amer.Chem.Soc., 67<1945>99, 101; Synthesis, 5, 1982, 397–399).

The formula (VI) provides a general definition of the O-alkyl-benzofuranone oximes required as starting materials for carrying out the process d) according to the invention. In this formula (VI), A, $R^1$, $R^2$, $R^3$ and $R^4$ each preferably or in particular have those meanings which have already been mentioned in connection with the description of the compounds of the formula (I) preparable according to the invention as being preferred or as being particularly preferred for A, $R^1$, $R^2$, $R^3$ and $R^4$.

The starting materials of the formula (VI) have not been disclosed before, and as novel compounds they also form part of the subject matter of the present application.

The O-alkyl-benzofurandione dioximes of the formula (VI) are obtained when (process f) ω-halogeno-2-hydroxyacetophenone oximes of the formula (IX)

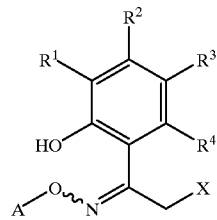

(IX)

in which

A, $R^1$, $R^2$, $R^3$ and $R^4$ are each as defined above, and

X represents halogen are reacted with a base, if appropriate in the presence of a diluent, or when (process g) benzofuranones of the formula (X)

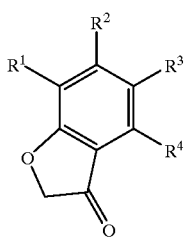

(X)

in which $R^1$, $R^2$, $R^3$ and $R^4$ are each as defined above are reacted with an alkoxyamine of the formula (VIII)—or an acid addition complex thereof— if appropriate in the presence of a diluent and, if appropriate, in the presence of an acid acceptor, or when (process h) benzofuranone oximes of the formula (XI)

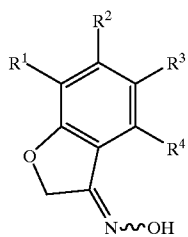

in which
R¹, R², R³ and R⁴ are each as defined above
are reacted with an alkylating agent of the formula

A—Y  (XII)

in which
A is as defined above and
Y represents halogen, alkylsulphonyloxy, alkoxysulphonyloxy or arylsulphonyloxy,
if appropriate in the presence of a diluent and, if appropriate, in the presence of a base.

The formula (IX) provides a general definition of the ω-halogeno-2-hydroxyacetophenone oximes required as starting materials for carrying out the process f) according to the invention. In this formula (IX), A, R¹, R², R³ and R⁴ each preferably or in particular have those meanings which have already been mentioned in connection with the description of the compounds of the formula (I) preparable according to the invention as being preferred or as being particularly preferred for A, R¹, R², R³ and R⁴. X represents halogen, preferably chlorine or bromine.

The starting materials of the formula (IX) have not been disclosed before, and as novel compounds they also form part of the subject matter of the present application.

The ω-halogeno-2-hydroxyacetophenone oximes of the formula (IX) are obtained when (process i) ω-halogeno-2-hydroxyacetophenones of the formula (XIII)

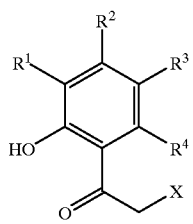

in which
R¹, R², R³, R⁴ and X are each as defined above
are reacted with an alkoxyamine of the formula (VIII)—or an acid addition complex thereof—
if appropriate in the presence of a diluent and, if appropriate, in the presence of an acid acceptor.

The formula (XIII) provides a general definition of the ω-halogeno-2-hydroxyacetophenones required as starting materials for carrying out the process i) according to the invention. In this formula (XIII), R¹, R², R³ and R⁴ each preferably or in particular have those meanings which have already been mentioned in connection with the description of the compounds of the formula (I) preparable according to the invention as being preferred or as being particularly preferred for R¹, R², R³ and R⁴. X represents halogen, preferably chlorine or bromine.

The ω-halogeno-2-hydroxyacetophenones of the formula (XIII) are known and can be prepared by known processes (J. Org. Chem. (1990), 55(14), 4371–7 and Synthesis (1988), (7), 545–6).

The formula (X) provides a general definition of the benzofuranones required as starting materials for carrying out the process g) according to the invention. In this formula (X), R¹, R², R³ and R⁴ each preferably or in particular have those meanings which have already been mentioned in connection with the description of the compounds of the formula (I) preparable according to the invention as being preferred or as being particularly preferred for R¹, R², R³ and R⁴.

The benzofuranones of the formula (X) are known and can be prepared by known processes (Friedlaender; Neudoerfer, Chem. Ber. 30 <1897>, 1081).

The formula (XI) provides a general definition of the benzofuranone oximes required as starting materials for carrying out the process h) according to the invention. In this formula (XI), R¹, R², R³ and R⁴ each preferably or in particular have those meanings which have already been mentioned in connection with the description of the compounds of the formula (I) preparable according to the invention as being preferred or as being particularly preferred for R¹, R², R³ and R⁴.

The benzofuranone oximes of the formula (XI) are known and can be prepared by known processes (cf. for example Stoermer, Bartsch, Chem. Ber., 33 <1900>, 3180).

The formula (XII) provides a general definition of the alkylating agents further required as starting materials for carrying out the process h) according to the invention. In this formula (XII), A preferably or in particular has those meanings which have already been mentioned in connection with the description of the compounds of the formula (I) preparable according to the invention as being preferred or as being particularly preferred for A. Y represents halogen, preferably chlorine, bromine or iodine, alkylsulphonyloxy, preferably methylsulphonyloxy, alkoxysulphonyloxy, preferably methoxysulphonyloxy, or arylsulphonyloxy, preferably 4-tolylsulphonyloxy.

The alkylating agents of the formula (XII) are known chemicals for synthesis.

The formula (VIII) provides a general definition of the alkoxyamines further required as starting materials for carrying out the processes e), g) and i) according to the invention. In this formula (VIII), A preferably or in particular has those meanings which have already been mentioned in connection with the description of the compounds of the formula (I) preparable according to the invention as being preferred or as being particularly preferred for A. Preferred acid addition complexes of the alkoxyamines of the formula (VIII) are their hydrochlorides, sulphates and hydrogen sulphates.

The alkoxyamines of the formula (VIII) and their acid addition complexes are known chemicals for synthesis.

The formula (IV) provides a general definition of the ethane derivatives further required as starting materials for carrying out the process b) according to the invention. In this formula (IV), Z¹, Z², Z³ and Z⁴ each preferably or in particular have those meanings which have already been mentioned in connection with the description of the compounds of the formula (I) preparable according to the invention as being preferred or as being particularly preferred for Z¹, Z², Z³ and Z4. Y¹ represents halogen, preferably chlorine, bromine or iodine, alkylsulphonyloxy, preferably methylsulphonyloxy, arylsulphonyloxy, preferably 4-tolylsulphonyloxy, or alkanoyloxy, preferably acetyloxy.

G represents hydrogen or is attached to $Y^1$ by a single bond where $Y^1$ represents oxygen and G represents carbonyl, or G and $Y^1$ together represent a single bond.

The ethane derivatives of the formula (IV) are known chemicals for synthesis.

If the process a) according to the invention is carried out in the presence of an acid, suitable diluents are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, dioxane, 1,2-dimethoxyethane, 1,2-diethoxyethane or anisole; esters such as methyl acetate or ethyl acetate, or sulphones such as sulpholane, and any mixtures of the diluents mentioned. Particularly preferred diluents are ethers such as diethyl ether, 1,2-diethoxyethane or anisole; aromatic hydrocarbons such as, for example, benzene, toluene or xylene.

If the process a) according to the invention is carried out in the presence of a base, suitable diluents are water and all organic solvents: These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water. Preferred diluents are water, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether; and mixtures thereof with water. Particularly preferred diluents in this case are water or alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water.

Suitable diluents for carrying out the process b) according to the invention are water and all organic solvents. These preferably include aliphatic, alicyclic or aromatic hydrocarbons such as, for example, petroleum ether, hexane, heptane, cyclohexane, methylcyclohexane, benzene, toluene, xylene or decal in; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water. Preferred diluents are water, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water. Particularly preferred diluents are water or alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water.

Suitable diluents for carrying out the process c) according to the invention are water and all organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, and mixtures thereof with water. Preferred diluents are water, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether; or nitriles such as acetonitrile, propionitrile, n- or i-butyronitrile or benzonitrile, and mixtures thereof with water.

Suitable diluents for carrying out the process d) according to the invention are water and all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; organic acids such as acetic acid; esters such as methyl acetate, ethyl acetate or butyl acetate; sulphoxides such as dimethyl sulphoxide, sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Suitable diluents for carrying out the processes e, g and i) according to the invention are all inert organic solvents. These preferably include aromatic hydrocarbons such as, for example, benzene, toluene or xylene; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; amides such as N,N-dimethylformamide, N,N-dimethylacetamide, N-methylformanilide, N-methylpyrrolidone or hexamethylphosphoric triamide; organic acids such as acetic acid; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water. Particularly preferred diluents are amides such as N,N-dimethylformamide, N,N-dimethylacetamide, N-methylformanilide, N-methylpyrrolidone or hexamethylphosphoric triamide; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water. Furthermore, particular preference is also given to two-phase mixtures such as, for example, water/toluene.

Suitable diluents for carrying out the process f) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decal in; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water, and two-phase mixtures such as, for example, water/toluene. Particularly preferred diluents are aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; and two-phase mixtures such as, for example, water/toluene.

Suitable diluents for carrying out the isomerization of the compounds of the formula (I) preparable according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, dioxane, tetrahydrofuran, 1,2-dimethoxyethane, 1,2-diethoxyethane or anisole; esters such as methyl acetate or ethyl acetate; sulphoxides such as dimethyl sulphoxide; or sulphones such as sulpholane.

The isomerization of the compounds of the formula (I) preparable according to the invention is, if appropriate, carried out in the presence of an acid. Suitable acids are all inorganic and organic protonic and Lewis acids. These include, for example, hydrogen chloride, hydrogen bromide, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide.

The process a) according to the invention is, if appropriate, carried out in the presence of an acid or a base. Suitable acids are all inorganic and organic protonic and Lewis acids, and also all polymeric acids. These include, for example, hydrogen chloride, hydrogen bromide, sulphuric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron(III) chloride, antimony pentachloride, acidic ion exchangers, acidic alumina and acidic silica gel. Preference is given to hydrogen chloride or hydrogen bromide. Suitable bases are all customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU). Particularly preferred bases are sodium methoxide, sodium ethoxide, potassium tert-butoxide, sodium hydroxide, potassium hydroxide, ammonium hydroxide, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process b) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU). Particularly preferred bases are sodium methoxide, sodium ethoxide, potassium tert-butoxide, sodium hydroxide, potassium hydroxide, ammonium hydroxide, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process c) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU). Particularly preferred bases are alkaline earth metal or alkali metal hydroxides, alkoxides, carbonates or bicarbonates such as, for example, sodium hydroxide, potassium hydroxide, ammonium hydroxide, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process d) according to the invention is, if appropriate, carried out in the presence of an acid or a base. Suitable acids are all inorganic and organic protonic acids. These include, for example, hydrogen chloride, sulphuric acid, phosphoric acid, formic acid, acetic acid, trifluoroacetic acid, methanesulphonic acid, trifluoromethanesulphonic acid or toluenesulphonic acid. Suitable bases are all customary inorganic or organic bases. These preferably include alkaline earth metal or alkali metal hydrides, hydroxides or alkoxides such as, for example, sodium hydride, sodium methoxide, sodium ethoxide, potassium tert-butoxide, sodium hydroxide or potassium hydroxide.

The processes e), g) and i) according to the invention are, if appropriate, carried out in the presence of a suitable acid acceptor. Suitable acid acceptors are all customary inorganic or organic bases. These preferably include alkaline earth metal or alkali metal hydroxides, alkoxides, acetates, carbonates or bicarbonates such as, for example, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

In the practice of the processes a) and b) according to the invention, the reaction temperatures may be varied over a relatively wide range. The reactions are generally carried out at temperatures from −20° C. to 100° C., preferably at temperatures from 0° C. to 80° C.

In the practice of the process c) according to the invention, the reaction temperatures may be varied over a relatively wide range. The reactions are generally carried out at temperatures from 0° C. to 150° C., preferably at temperatures from 20° C. to 100° C.

In the practice of the processes e), g) and i) according to the invention, the reaction temperatures may be varied over a relatively wide range. The reactions are generally carried out at temperatures from 0° C. to 150° C., preferably at temperatures from 0° C. to 80° C.

In the practice of the process d) according to the invention, the reaction temperatures may be varied over a relatively wide range. The reactions are generally carried out at temperatures from −20° C. to 150° C., preferably at temperatures from 0° C. to 100° C.

In the practice of the process f) according to the invention, the reaction temperatures may be varied over a relatively wide range. The reactions are generally carried out at temperatures from 0° C. to 200° C., preferably at temperatures from 20° C. to 150° C.

In the practice of the process a) according to the invention for preparing the compounds of the formula (I), in general 1 to 15 mol, preferably 2 to 6 mol, of base are employed per mole of the O-hydroxyethyl-O'-alkyl-benzofurandione dioxime of the formula (II).

In the practice of the process b) according to the invention for preparing the compounds of the formula (II), in general 1 to 15 mol, preferably 3 to 6 mol, of ethane derivative of the formula (IV) are employed per mole of the O-alkyl-benzofurandione dioxime of the formula (III).

In the practice of the process c) according to the invention for preparing the compounds of the formula (III), in general 1 to 15 mol, preferably 2 to 8 mol, of base are employed per mole of the ω-nitro-2-hydroxyacetophenone oxime of the formula (V).

In the practice of the process d) according to the invention for preparing the compounds of the formula (III), in general 1 to 5 mol, preferably 1 to 3 mol, of alkali metal nitrite or alkyl nitrite are employed per mole of the O-alkyl-benzofuranone oxime of the formula (VI).

In the practice of the processes e), g) and i) according to the invention for preparing the compounds of the formula (V), (VI) and (IX), respectively, in general 1 to 15 mol, preferably 1 to 8 mol, of the alkoxyamine of the formula (VIII)—or an acid addition complex thereof—are employed per mole of the ω-nitro-2-hydroxyacetophenone of the formula (VII), the benzofuranone of the formula (X) and the ω-halogeno-2-hydroxyacetophenone of the formula (XIII), respectively.

In the practice of the process f) according to the invention for preparing the compounds of the formula (VI), in general 1 to 15 mol, preferably 1 to 5 mol, of base are employed per mole of the ω-halogeno-2-hydroxyacetophenone oxime of the formula (IX).

The processes a) to i) according to the invention are generally carried out at atmospheric pressure. However, it is also possible to carry out the processes at elevated or reduced pressure—in general between 0.1 bar and 10 bar.

In a preferred process variant (A), an ω-nitro-2-hydroxyacetophenone of the formula (VII) is converted into an ω-nitro-2-hydroxyacetophenone oxime of the formula (V) by reaction with an alkoxyamine of the formula (VIII)—or an acid addition complex thereof—if appropriate in a buffer system such as, for example, sodium acetate/acetic acid, as described in process e). Compound (V) is reacted with a base, for example an aqueous sodium bicarbonate solution, to give an O-alkyl-benzofurandione dioxime of the formula (III). The O-alkyl-benzofurandione dioxime of the formula (III) is reacted in basic solution, for example an aqueous alkali metal hydroxide solution, with an ethane derivative of the formula (IV) to give an O-hydroxyethyl-O'-alkyl-benzofurandione dioxime of the formula (II) which, preferably without work-up, reacts further in the basic solution to give the desired 3-(1-hydroxyphenyl-1-alkoximinomethyl)dioxazine. This is, if appropriate, isomerized to the desired E isomer, for example by treatment with an acid, such as hydrogen chloride, in an organic solvent, such as ethyl acetate.

In a further preferred process variant (B), an ω-halogeno-2-hydroxyacetophenone of the formula (XIII) is converted into an ωhalogeno-2-hydroxyacetophenone oxime of the formula (IX) by reaction with an alkoxyamine of the formula (VIII)—or an acid addition complex thereof—if appropriate in a buffer system such as, for example, sodium acetate/acetic acid, as described in process i). The compound of the formula (IX) is cyclized by treatment with a base, for example with sodium bicarbonate in the water/methyl t-butyl ether system, to give an O-alkyl-benzofuranone oxime of the formula (VI). On treatment with an alkali metal nitrite or alkyl nitrite in acidic or basic solution, the O-alkyl-benzofuranone oxime of the formula (VI) affords an O-alkyl-benzofurandione dioxime of the formula (III). The O-alkyl-benzofurandione dioxime of the formula (III) is reacted in basic solution, for example an aqueous alkali metal hydroxide solution, with an ethane derivative of the formula (IV) to give an O-hydroxyethyl-O'-alkyl-benzofurandione dioxime of the formula (II) which, preferably without work-up, reacts further in the basic solution to give the desired 3-(1-hydroxyphenyl-1-alkoximinomethyl) dioxazine. This is, if appropriate, isomerized to the desired E isomer, for example by treatment with an acid, such as hydrogen chloride, in an organic solvent, such as ethyl acetate.

In a third preferred process variant (C), a benzofuranone of the formula (X) is converted into an O-alkylbenzofuranone oxime of the formula (VI) by reaction with an alkoxyamine of the formula (VIII)—or an acid addition complex thereof—if appropriate in a buffer system such as, for example, sodium acetate/acetic acid, as described in process g). On treatment with an alkali metal nitrite or alkyl nitrite in acidic or basic solution, the O-alkyl-benzofuranone oxime of the formula (VI) affords an O-alkyl-benzofuranonedione dioxime of the formula (III). The O-alkyl-benzofurandione dioxime of the formula (III) is reacted in basic solution, for example an aqueous alkali metal hydroxide solution, with an ethane derivative of the formula (IV) to give an O-hydroxyethyl-O'-alkyl-benzofurandione dioxime of the formula (II) which, preferably without work-up, reacts further in the basic solution to give the desired 3-(1-hydroxyphenyl-1-alkoximinomethyl) dioxazine. This is, if appropriate, isomerized to the desired E isomer, for example by treatment with an acid, such as hydrogen chloride, in an organic solvent, such as ethyl acetate.

It is very surprising that the processes according to the invention, in particular when combined, yield high purity products in high yields. It is particularly surprising that compounds of the general formula (V) readily cyclize with elimination of water even in the presence of water at temperatures as low as room temperature on treatment with bases to give high yields of compounds of the formula (III) and can be isolated in high purity simply by filtration. According to the known literature, under these conditions only a deprotonation of the compounds of the formula (V) was to be expected. Furthermore, it is particularly surprising that the compounds of the formula (III) can be reacted with epoxides under alkaline conditions, without any problems, to give compounds of the formula (II) which in turn, if appropriate even without work-up, immediately cyclize to the desired 3-(1-hydroxyphenyl-1-alkoximinomethyl) dioxazines. Chem. Ber. 1902, 1640, for example, describes that benzofurandione monooximes are cleaved to give salicylic acid derivatives or hydroxyphenylglyoxalic acid derivatives by treatment both with acids and with bases. Thus, it would have been more likely to expect the compounds of the formula (III) to decompose likewise under the given reaction conditions. The smooth nitrosation of the compounds of the formula (VI) (process d) is also surprising, since a nitrosation of methyl or methylene groups which are located ax to oximes, in contrast to methyl or methylene groups which are located α to keto groups, has not been described before.

The processes according to the invention have a number of advantages. Thus, they allow the preparation of a large quantity of 3-(1-hydroxyphenyl-1-alkoximinomethyl) dioxazines in high yields and high purities. It is a further advantage that the ethane derivatives of the formula (IV), the ω-nitro-2-hydroxyacetophenones of the formula (VII), the benzofuranones of the formula (X), and the ω-halogeno-2-hydroxyacetophenones of the formula (XIII) required as starting materials are easily obtainable at low cost, even in larger amounts.

PREPARATION AND PROCESS EXAMPLES

Example 1

Process variant (A)

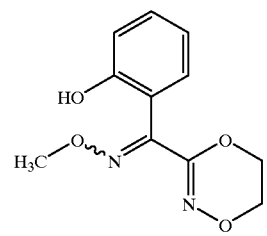

(I-1)

Step 1
Compound (V-1)

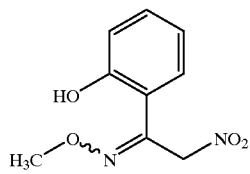

Process e)

At 20° C., 73.5 g (0.88 mol) of methoxyamine hydrochloride are added to a solution of 80.0 g (0.44 mol) of o-hydroxy-ω-nitroacetophenone in 500 ml of methanol, and the mixture is stirred at 45 to 50° C. for 8 to 12 hours. The solution is cooled to 20° C., poured into 1 l of ice-water and stirred for one hour. The crystalline product is filtered off and washed with 500 ml of water a little at a time and dried at 40° C. in a vacuum drying cabinet. 72 g (74.6% of theory) of 1-(2-hydroxyphenyl)-2-nitro-ethanone O-methyl-oxime are obtained as a mixture of stereoisomers.

HPLC: logP=1.87 (12.3%), 2.27 (83.5%).

Step 2
Compound (III-1)

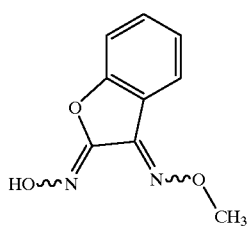

Process c)

71.8 g of 1-(2-hydroxy-phenyl)-2-nitro-ethanone O-methyl-oxime are added to a solution of 121 g (0.342 mol) of sodium bicarbonate in 700 ml of water. Within 30 minutes, the mixture is heated to 90–95° C., on which undissolved starting material melts and reacts and the product crystallizes out. The mixture is cooled to 20° C. and the product is filtered off, washed with 500 ml of water a little at a time and air-dried. 57.4 g (91.3% of theory) of benzofuran-2,3-dione 3-(O-methyl-oxime) 2-oxime are obtained as a mixture of two stereoisomers.

HPLC: logP=1.56 (28.4%), 1.72 (71.6%).

Step 3
Compound (II-1)

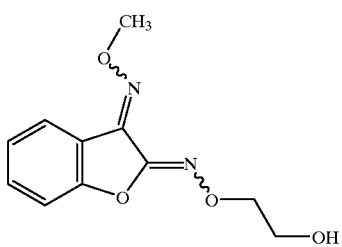

Process b)

At 20° C., 264.3 g (6.0 mol) of ethylene oxide are passed into a solution of 192.2 g (1.0 mol) of benzofuran-2,3-dione 3-(O-methyl-oxime) 2-oxime in 2 l of water over a period of 85 minutes. The solution is cooled to 5° C. and 70 g (1.06 mol) of sodium hydroxide pellets are added, on which the temperature increases to 10° C. The mixture is stirred without further cooling for another 165 minutes and the precipitate that has formed is filtered off with suction, washed with 500 ml of ice-water a little at a time and dried at 40° C. in a vacuum drying cabinet. 143.0 g (61% of theory) of benzofuran-2,3-dione 2-[O-(2-hydroxy-ethyl)-oxime] 3-(O-methyl-oxime) are obtained as a mixture of two stereoisomers.

HPLC: logP=1.65 (0.5%), 1.79 (99.5%).

Step 4
Compound (I-1)

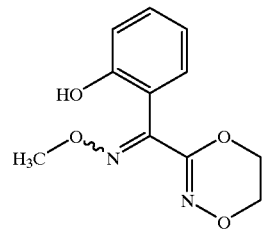

Process a)

A solution of 25.6 g (0.1084 mol) of benzofuran-2,3-dione 2-[O-(2-hydroxy-ethyl)oxime] 3-(O-methyl-oxime) and 14.2 g (0.216 mol) of potassium hydroxide pellets in 250 ml of water is stirred at 60° C. for 195 minutes. The solution is cooled to 10° C. and acidified to pH 5–6 with glacial acetic acid. The crystalline product is filtered off with suction, washed with 200 ml of water a little at a time and dried at 45° C. in a vacuum drying oven. 17.7 g (67.7% of theory) of E-(5,6-dihydro-[1,4,2]dioxazin-3-yl)-(2-hydroxyphenyl)-methanone O-methyl-oxime are obtained.

HPLC: logP=1.22.

Example 2

Compound (I-1)

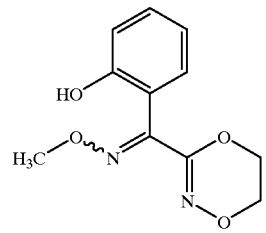

One-pot variant of processes a) and b)

At 20° C., 19.8 g (0.3 mol) of potassium hydroxide pellets are added to a suspension of 38.4 g (0.2 mol) of benzofuran-2,3-dione 3-(O-methyl-oxime) 2-oxime in 400 ml of water and the mixture was stirred for 30 minutes, on which a solution forms. At 20° C., 17.6 g (0.4 mol) of ethylene oxide are introduced over a period of 75 minutes, and the mixture is stirred at 20° C. overnight, on which a precipitate forms. The mixture is then stirred at 60° C. for 11 hours, on which the precipitate redissolves. The solution is cooled and acidified to pH 5–6 with glacial acetic acid. The crystalline product is filtered off with suction, washed with 300 ml of water a little at a time and dried at 45° C. in a vacuum drying cabinet. 19.6 g (39.3% of theory) of (5,6-dihydro-[1,4,2] dioxazin-3-yl)-(2-hydroxy-phenyl)-methane O-methyl-oxime are obtained.

HPLC: logP=1.24 (E isomer 94.2%); 2.05 (Z isomer 0.6%).

Example 3

Compound (I-1)

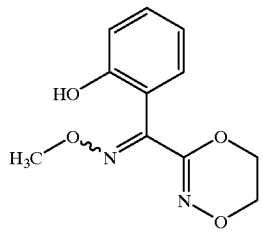

Isomerization 112 g of hydrogen chloride are introduced into a solution of 806 g (4.19 mol) of (5,6-dihydro-[1,4,2]dioxazin-3-yl)-(2-hydroxy-phenyl)-methanone O-methyl-oxime (33.3% of Z isomer, 66.6% of E isomer) over a period of 60 minutes, on which the solution warms from 20° C. to 27° C. The mixture is stirred at 20° C. for another 18 hours and subsequently concentrated under reduced pressure. The residue is dried at 40° C. in a vacuum drying cabinet. 806 g (100% of theory) of (5,6-dihydro-[1,4,2]dioxazin-3-yl)-(2-hydroxy-phenyl)-methanone O-methyl-oxime with an E isomer content of 94.8% (HPLC) are obtained.

Example 4

Compound (III-1)

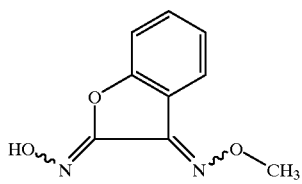

Process d)

3.92 g (0.035 mol) of potassium tert-butoxide are dissolved in 40 ml of tert-butanol. A solution of 5.7 g (0.035 mol) of benzofuran-3-one O-methyl-oxime and 7.2 g (0.07 mol) of tert-butyl nitrite in 10 ml of tert-butanol is added to this solution. The mixture is stirred without cooling for two hours and then admixed with 20 ml of 2N aqueous hydrochloric acid. The crystalline product is filtered off, washed repeatedly with water and dried in a desiccator. 3.19 g (47.1% of theory) of benzofuran-2,3-dione 3-(O-methyl-oxime) 2-oxime are obtained as a mixture of two stereoisomers comprising 86.33% of isomer A and 12.98% of isomer B (HPLC).

$^1$H NMR spectrum (DMSO-$d_6$/TMS): δ=4.10 (3H, isomer B); 4.11 (3H; isomer A); 7.21/7.24/7.26 (1H); 7.31/7.34 (1H); 7.51/7.53/7.56 (1H); 7.63/7.65 (1H, isomer B) 8.02/ 8.05 (1H, isomer A); 11.36 (1H, isomer A); 11.75 (1H, isomer B) ppm.

Identical results are obtained when butyl acetate is used instead of tert-butanol.

Example 5

Compound (III-1)

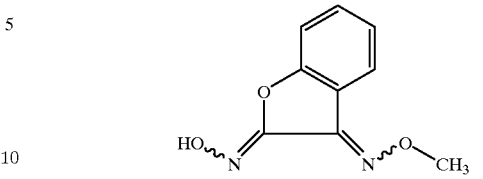

Process d)

At −10° C., 2 g (0.019 mol) of tert-butyl nitrite are added dropwise to 30 ml of ethyl acetate which is saturated with dry hydrogen chloride, and the mixture is stirred at this temperature for 15 minutes. At −10° C., 1.6 g (0.0098 mol) of benzofuran-3-one O-methyl-oxime dissolved in 5 ml of ethyl acetate are then added, the temperature is allowed to increase to 0° C. and the mixture is stirred at this temperature for 30 minutes. The crystalline product is filtered off, affording 1.08 g of crystalline benzofuran-2,3-dione 3-(O-methyl-oxime) 2-oxime as a mixture of two stereoisomers comprising, according to HPLC analysis, 54.7% (56% of theory) of isomer B and 42.9% of isomer A.

$^1$H NMR spectrum (CDCl$_3$/TMS): δ=4.10 (3H, isomer B); 4.11 (3H, isomer A); 7.21–7.26 (1H); 7.31–7.35 (1H); 7.5–7.65 (2H, isomer B+1H, isomer A); 8.02–8.05 (1H, isomer A); 11.36 (1H, isomer A); 11.75 (1H, isomer B) ppm.

5-Methylbenzofuran-2,3-dione 3-(O-methyl-oxime) 2-oxime (III-2) was obtained in a similar fashion.

$^1$H NMR spectrum (CDCl$_3$/TMS): δ=2.24 (3H, isomer B); 2.25 (3H, isomer A) ppm.

Example 6

Compound (VI-1)

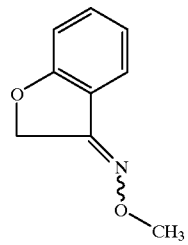

Process f)

74 g (0.303 mol) of 2-bromo-1-(2-hydroxy-phenyl)-ethanone O-methyl-oxime are dissolved in 350 ml of tert-butyl methyl ether and heated under reflux with a solution of 40 g (0.377 mol) of sodium carbonate in 400 ml of water with vigorous stirring for 5 days. The organic phase is separated off and dried over sodium sulphate and the solvent is distilled off under reduced pressure, affording 45.5 g (82.8% of theory, 90% of Z isomer according to HPLC analysis) of crude benzofuran-3-one O-methyl-oxime.

$^1$H NMR spectrum (DMSO-$d_6$/TMS): δ=3.93 (3H); 5.16 (2H); 7.0–7.07 (2H); 7.39–7.45 (1H); 7.54–7.57 (1H) ppm.

5-Methylbenzofuran-3-one O-methyl-oxime (VI-2) was obtained in a similar fashion.

GC/MS: M$^+$=177; HPLC: logP=2.88.

Example 7

Compound (VI-1)

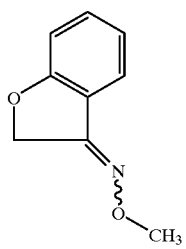

Process g)

6.7 g (0.05 mol) of benzofuran-3-one together with 4.2 g (0.05 mol) of O-methylhydroxylamine hydrochloride and 4.1 g (0.05 mol) of sodium acetate in 50 ml of methanol are heated under reflux for 3 hours. The solvent is distilled off under reduced pressure and the reaction mixture is poured into water and extracted with ethyl acetate. The organic phase is washed with saturated aqueous sodium carbonate solution. The organic phase is dried over sodium sulphate and the solvent is distilled off under reduced pressure. 7.27 g (89.2% of theory) of crude benzofuran-3-one O-methyl-oxime are obtained. For analysis, the crude product is distilled at 2 torr and 70° C. using a Kugelrohr. An oil is obtained which, both according to NMR analysis and according to HPLC analysis, comprises two stereoisomers (79% of isomer B and 21% of isomer A).

$^1$H-NMR spectrum (DMSO-$d_6$/TMS): $\delta$=3.93 (3H, isomer B); 3.93 (3H, isomer A); 5.11 (2H, isomer A); 5.16 (2H, isomer B); 7.0–7.07 (2H); 7.39–7.45 (1H); 7.54/7.57 (1H, isomer B); 7.95–8.02 (1H, isomer A) ppm.

Example 8

Compound (VI-1)

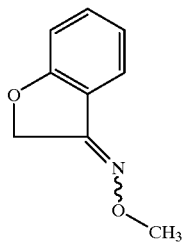

Process h)

3.7 g of benzofuran-3-one oxime are dissolved in 15 ml of dimethylformamide. At 20° C., 1 g of sodium hydride (60%) is added and the mixture is stirred until the evolution of gas ceases. 3.15 g of dimethyl sulphate are then added dropwise and the mixture is stirred at 20° C. for 24 hours. The reaction mixture is poured into water, extracted with ethyl acetate, the organic phase is dried over sodium sulphate and the solvent is distilled off under reduced pressure. The residue is chromatographed over silica gel using n-hexane/acetone (4:1). 1.7 g (42% of theory) of benzofuran-3-one O-methyl-oxime are obtained as an oil.

$^1$H-NMR spectrum (DMSO-$d_6$/TMS): $\delta$=3.93 (3H); 5.16 (2H); 7.0–7.07 (2H); 7.39–7.45 (1H); 7.54/7.57 (1H) ppm.

Example 9

Compound (IX-1)

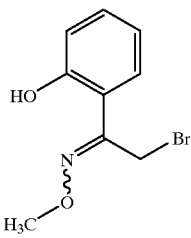

Process i)

107.5 g (0.5 mol) of ω-bromo-2-hydroxy-acetophenone in 500 ml of methanol together with 41.75 g (0.5 mol) of O-methylhydroxylamine hydrochloride are heated under reflux for 4 hours. The methanol is distilled off under reduced pressure and the residue is admixed with 500 ml of water and extracted with 4 times 100 ml of ethyl acetate. The organic phase is dried over sodium sulphate and the solvent is distilled off under reduced pressure. At 0° C., the residue is stirred with petroleum ether, affording 74 g (52% of theory) of crystalline 2-bromo-1-(2-hydroxy-phenyl)-ethanone O-methyl-oxime as a mixture of two stereoisomers (53% of isomer B and 33% of isomer A).

$^1$H NMR spectrum (CDCl$_3$/TMS): $\delta$=3.98 (3H, isomer B); 3.99 (3H, isomer A); 4.53 (3H, isomer A); 4.69 (3H, isomer B); 6.85–6.93 (2H); 7.26–7.35 (2H); 10.21 (1H, isomer B); 10.25 (1H, isomer A) ppm.

2-Chloro-1-(2-hydroxy-5-methyl-phenyl)-ethanone O-methyl-oxime (IX-2) was obtained in a similar fashion.

$^1$H NMR spectrum (CDCl$_3$/TMS): $\delta$=2.32 (s, 3H); 4.08 (s, 3H) ppm.

Similar to Examples 1 and 2, and according to the general description of the process a) according to the invention, the compounds of the formula (I-a) listed in Table 1 were obtained:

TABLE 1

(I-a)

| Compound | $R^3$ | $Z^1$ | $Z^2$ | mp (° C.) | log P | NMR* |
|---|---|---|---|---|---|---|
| 2 | —C$_2$H$_5$ | —H | —H | | 1.88 | 1.23(m, 3H); 2.62(m, 2H; 4.10(s, 3H); 4.21(m, 2H); 4.49(m, 2H) |
| 3 | —CH$_3$ | —H | —H | | 1.52 | 2.29(s, 3H); 4.10(s, 3H); 4.21(m, 2H); 4.49(m, 2H) |
| 4 | —H | —CH$_3$ | —H | 136 | 1.49 | |
| 5 | —H | —C$_2$H$_5$ | —H | 134 | 1.82 | |
| 6 | —H | —CH$_3$ | —CH$_3$ | | 1.68 | |

*The $^1$H NMR spectra were recorded in deutrochloroform (CDCl$_3$) or hexadeuterodimethyl sulphoxide (DMSO-$d_6$) using tetramethylsilane (TMS) as internal standard. Stated is the chemical shift as $\delta$ value in ppm.

Similar to Example 1, compound (II-1), and according to the general description of the process b) according to the invention, the compounds of the formula (II-a) listed in Table 2 were obtained:

TABLE 2

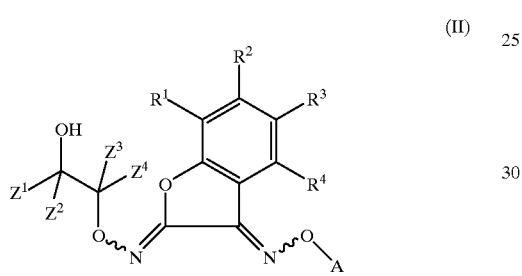

(II-a)

| Compound | R³ | Z¹ | Z² | mp. (° C.) | log P |
|---|---|---|---|---|---|
| (II-2) | —CH₃ | —H | —H | | 2.10 |
| (II-3) | —C₂H₅ | —H | —H | | 2.46 |
| (II-4) | —H | —H | —CH₃ | 81 | 2.04 |
| (II-5) | —H | —CH₃ | —CH₃ | 72 | 2.27 |
| (II-6) | —H | —H | —C₂H₅ | 74 | 2.39 |

We claim:
1. A compound of the formula (II):

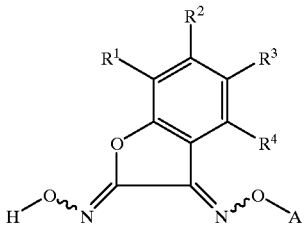

(II)

in which
A represents alkyl;
$R^1$, $R^2$, $R^3$ and $R^4$ independently represent hydrogen, halogen, cyano, nitro, or in each case optionally halogen-substituted alkyl, alkoxy, alkylthio, alkylsulphinyl or alkylsulphonyl; and
$Z^1$, $Z^2$, $Z^3$ and $Z^4$ independently represent hydrogen, alkyl, halogenoalkyl or hydroxyalkyl; or
$Z^1$ and $Z^2$, or $Z^1$ and $Z^3$, or $Z^3$ and $Z^4$ together with the carbon atoms to which they are attached form a cycloaliphatic ring.

2. A compound of the formula (II) according to claim 1, in which
A represents methyl, ethyl, n- or i-propyl;
$R^1$, $R^2$, $R^3$ and $R^4$ independently represent hydrogen, halogen, cyano, nitro, or represents alkyl, alkoxy, alkylthio, alkylsulphinyl or alkylsulphonyl, each of which has 1 to 6 carbon atoms, and each of which is optionally substituted by 1 to 5 identical or different halogen atoms; and
$Z^1$, $Z^2$, $Z^3$ and $Z^4$ independently represent hydrogen, or represent alkyl or hydroxyalkyl, each of which has 1 to 4 carbon atoms, or represent halogenoalkyl, which has 1 to 4 carbon atoms and 1 to 5 identical or different halogen atoms; or
$Z^1$ and $Z^2$, or $Z^1$ and $Z^3$, or $Z^3$ and $Z^4$ together with the carbon atoms to which they are attached form a cycloaliphatic ring, which has 5 to 7 carbon atoms.

3. A compound of the formula (II) according to claim 1, in which
A represents methyl or ethyl;

$R^1$, $R^2$, $R^3$ and $R^4$ independently represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl; and
$Z^1$, $Z^2$, $Z^3$ and $Z^4$ independently represent hydrogen, or represent methyl, ethyl, n- or i-propyl, n-, i-, s- or t-butyl, hydroxymethyl, trifluoromethyl or trifluoroethyl; or
$Z^1$ and $Z^2$, or $Z^1$ and $Z^3$, or $Z^3$ and $Z^4$ together with the carbon atoms to which they are attached form a cycloaliphatic ring, which has 5 to 7 carbon atoms.

4. Process for preparing a compound of the formula (II) according to claim 1, said process comprising reacting an O-alkyl-benzofurandione dioxime of the formula (III):

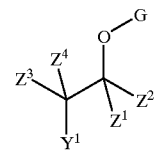

(III)

in which
A represents alkyl; and
$R^1$, $R^2$, $R^3$ and $R^4$ independently represent hydrogen, halogen, cyano, nitro, or in each case optionally halogen-substituted alkyl, alkoxy, alkylthio, alkylsulphinyl or alkylsulphonyl;
with an ethane derivative of the formula (IV):

(IV)

in which
$Z^1$, $Z^2$, $Z^3$ and $Z^4$ independently represent hydrogen, alkyl, halogenoalkyl or hydroxyalkyl; or
$Z^1$ and $Z^2$, or $Z^1$ and $Z^3$, or $Z^3$ and $Z^4$ together with the carbon atoms to which they are attached form a cycloaliphatic ring; and
a) $Y^1$ represents halogen, alkylsulphonyloxy, arylsulphonyloxy or alkanoyloxy; and
G represents hydrogen; or
b) $Y^1$ represents oxygen; and
G represents —CO—; and
$Y^1$ and G are linked by a single bond; or
c) $Y^1$ and C together represent a single bond;
optionally in the presence of a diluent, and optionally in the presence of a base.

* * * * *